United States Patent
Lin et al.

(10) Patent No.: US 9,113,988 B2
(45) Date of Patent: *Aug. 25, 2015

(54) METHOD FOR INSERTING MEDICINE INTO ANIMAL TISSUE

(75) Inventors: Kwan Ku Lin, Pasadena, CA (US); Philip S. Yuan, Fayetteville, NY (US)

(73) Assignee: Crosstrees Medical, Inc., Boulder, CO (US)

(*) Notice: Subject to any disclaimer, the term of this patent is extended or adjusted under 35 U.S.C. 154(b) by 1855 days.

This patent is subject to a terminal disclaimer.

(21) Appl. No.: 11/674,087

(22) Filed: Feb. 12, 2007

(65) Prior Publication Data

US 2007/0142765 A1    Jun. 21, 2007

Related U.S. Application Data

(63) Continuation of application No. 10/652,470, filed on Sep. 2, 2003, now Pat. No. 7,175,628.

(30) Foreign Application Priority Data

May 21, 2003    (TW) ................................ 92113771 A

(51) Int. Cl.
   *A61M 31/00*    (2006.01)
   *A61M 37/00*    (2006.01)
   (Continued)

(52) U.S. Cl.
   CPC .............. *A61D 7/00* (2013.01); *A61B 17/8833* (2013.01); *A61F 2/441* (2013.01); *A61F 2/4601* (2013.01);
   (Continued)

(58) Field of Classification Search
   CPC ........... A61B 17/8805; A61B 17/7097; A61B 2017/0256; A61B 17/7061; A61B 17/8833; A61B 17/885; A61F 2/4601; A61F 2/441; A61F 2002/2835; A61F 2002/30581; A61F 10/1003

USPC ............. 604/57–64, 93.01, 500, 502; 606/86, 606/92, 93, 94; 623/17.12
   See application file for complete search history.

(56) References Cited

U.S. PATENT DOCUMENTS 3,834,394 A    9/1974    Hunter et al.
3,993,080 A *  11/1976   Loseff .............................. 604/28
(Continued)

FOREIGN PATENT DOCUMENTS

EP    1 495 729 A1    1/2005
EP    1 495 730 A1    1/2005
(Continued)

OTHER PUBLICATIONS

International Search Report and Written Opinion for International Application PCT/US06/61207, mailed Oct. 5, 2007.
(Continued)

*Primary Examiner* — Theodore Stigell
*Assistant Examiner* — Lauren M Peng

(57) ABSTRACT

An extractable device is used to insert a medicinal filling into an animal tissue. The device comprises a filling member and a pasty medicine. The filling member is made of a flexible and hermetic wall and is provided with a holding portion and an injection port via which the pasty medicine is injected into the holding portion after the filling member is inserted into the animal tissue. The holding portion is provided with an opening which is releasably lashed by one end of one or more threads so as to make the opening leakproof. Upon completion of solidification of the pasty medicine in the holding portion of the filling member, other end of the thread is pulled to unlash the opening of the holding portion, thereby enabling the filling member to be extracted from the animal tissue so as to leave only the medicine in the animal tissue.

22 Claims, 13 Drawing Sheets

(51) Int. Cl.

| | |
|---|---|
| *A61D 7/00* | (2006.01) |
| *A61B 17/88* | (2006.01) |
| *A61F 2/44* | (2006.01) |
| *A61F 2/46* | (2006.01) |
| *A61B 17/70* | (2006.01) |
| *A61B 17/02* | (2006.01) |
| *A61F 2/30* | (2006.01) |
| *A61F 2/28* | (2006.01) |

(52) U.S. Cl.
CPC ............ *A61M 31/00* (2013.01); *A61B 17/7061* (2013.01); *A61B 17/7097* (2013.01); *A61B 17/8805* (2013.01); *A61B 17/885* (2013.01); *A61B 2017/0256* (2013.01); *A61F 2002/2835* (2013.01); *A61F 2002/30581* (2013.01); *A61M 2210/1003* (2013.01)

(56) References Cited

U.S. PATENT DOCUMENTS

| | | | |
|---|---|---|---|
| 4,488,549 A | 12/1984 | Lee et al. | |
| 4,625,722 A | 12/1986 | Murray | |
| 4,969,888 A | 11/1990 | Scholten et al. | |
| 4,983,168 A | 1/1991 | Moorehead | |
| 5,015,255 A | 5/1991 | Kuslich | |
| 5,017,175 A | 5/1991 | Klusmire | |
| 5,054,492 A | 10/1991 | Scribner et al. | |
| 5,062,845 A | 11/1991 | Kuslich et al. | |
| 5,108,404 A | 4/1992 | Scholten et al. | |
| 5,549,679 A * | 8/1996 | Kuslich | 623/17.12 |
| 5,632,275 A | 5/1997 | Browne et al. | |
| 5,697,889 A | 12/1997 | Slotman et al. | |
| 5,744,958 A | 4/1998 | Werne | |
| 5,782,764 A | 7/1998 | Werne | |
| 5,827,289 A | 10/1998 | Reiley et al. | |
| 5,972,015 A | 10/1999 | Scribner et al. | |
| 5,976,186 A | 11/1999 | Bao et al. | |
| 6,017,366 A | 1/2000 | Berman | |
| 6,048,346 A | 4/2000 | Reiley et al. | |
| 6,053,904 A | 4/2000 | Scribner et al. | |
| 6,066,154 A | 5/2000 | Reiley et al. | |
| 6,146,422 A | 11/2000 | Lawson | |
| 6,235,043 B1 | 5/2001 | Reiley et al. | |
| 6,241,734 B1 | 6/2001 | Scribner et al. | |
| 6,245,107 B1 | 6/2001 | Ferree | |
| 6,248,110 B1 | 6/2001 | Reiley et al. | |
| 6,383,188 B2 | 5/2002 | Kuslich et al. | |
| 6,402,784 B1 | 6/2002 | Wardlaw | |
| 6,440,138 B1 | 8/2002 | Reiley et al. | |
| 6,443,988 B2 | 9/2002 | Felt et al. | |
| 6,488,710 B2 | 12/2002 | Besselink | |
| 6,508,839 B1 | 1/2003 | Lambrecht et al. | |
| 6,533,817 B1 | 3/2003 | Norton et al. | |
| 6,558,390 B2 | 5/2003 | Cragg | |
| 6,575,919 B1 | 6/2003 | Reiley et al. | |
| 6,602,291 B1 | 8/2003 | Ray et al. | |
| 6,607,544 B1 | 8/2003 | Boucher et al. | |
| 6,632,235 B2 | 10/2003 | Weikel et al. | |
| 6,641,587 B2 | 11/2003 | Scribner et al. | |
| 6,645,213 B2 | 11/2003 | Scribner et al. | |
| 6,706,069 B2 | 3/2004 | Berger | |
| 6,712,819 B2 | 3/2004 | Zucherman et al. | |
| 6,716,216 B1 | 4/2004 | Boucher et al. | |
| 6,719,773 B1 | 4/2004 | Boucher et al. | |
| 6,726,691 B2 | 4/2004 | Osorio et al. | |
| 6,740,093 B2 | 5/2004 | Hochschuler et al. | |
| 6,746,451 B2 | 6/2004 | Middleton et al. | |
| 6,923,813 B2 | 8/2005 | Phillips et al. | |
| 6,960,215 B2 | 11/2005 | Olson, Jr. et al. | |
| 6,979,341 B2 | 12/2005 | Scribner et al. | |
| 7,044,954 B2 | 5/2006 | Reiley et al. | |
| 7,063,705 B2 | 6/2006 | Young et al. | |
| 7,081,122 B1 | 7/2006 | Reiley et al. | |
| 7,153,306 B2 | 12/2006 | Ralph et al. | |
| 7,166,110 B2 | 1/2007 | Yundt | |
| 7,166,121 B2 | 1/2007 | Reiley et al. | |
| 7,175,627 B2 | 2/2007 | Lin et al. | |
| 7,175,629 B2 | 2/2007 | Lin et al. | |
| 7,226,481 B2 | 6/2007 | Kuslich | |
| 7,241,303 B2 | 7/2007 | Reiss et al. | |
| 7,261,720 B2 | 8/2007 | Stevens et al. | |
| 7,429,264 B2 | 9/2008 | Melkent et al. | |
| 7,465,318 B2 | 12/2008 | Sennett et al. | |
| 7,674,265 B2 | 3/2010 | Smith et al. | |
| 7,749,230 B2 | 7/2010 | Yuan et al. | |
| 8,961,553 B2 | 2/2015 | Hollowell et al. | |
| 2002/0026195 A1 | 2/2002 | Layne et al. | |
| 2002/0156482 A1* | 10/2002 | Scribner et al. | 606/92 |
| 2003/0050644 A1 | 3/2003 | Boucher et al. | |
| 2004/0006347 A1 | 1/2004 | Sproul | |
| 2004/0024410 A1 | 2/2004 | Olson, Jr. et al. | |
| 2004/0059417 A1* | 3/2004 | Smith et al. | 623/17.11 |
| 2004/0073308 A1 | 4/2004 | Kuslich et al. | |
| 2004/0102774 A1 | 5/2004 | Trieu | |
| 2004/0106999 A1 | 6/2004 | Mathews | |
| 2004/0122455 A1 | 6/2004 | Lin | |
| 2004/0186481 A1 | 9/2004 | Lin et al. | |
| 2004/0210297 A1 | 10/2004 | Lin et al. | |
| 2005/0015097 A1 | 1/2005 | Mujwid et al. | |
| 2005/0065609 A1* | 3/2005 | Wardlaw | 623/17.12 |
| 2005/0090852 A1 | 4/2005 | Layne et al. | |
| 2005/0119662 A1 | 6/2005 | Reiley et al. | |
| 2005/0228397 A1 | 10/2005 | Malandain et al. | |
| 2005/0267483 A1 | 12/2005 | Middleton | |
| 2006/0079905 A1 | 4/2006 | Beyar et al. | |
| 2006/0155296 A1 | 7/2006 | Richter | |
| 2006/0229625 A1 | 10/2006 | Truckai et al. | |
| 2006/0247648 A1 | 11/2006 | Serbousek | |
| 2006/0271057 A1 | 11/2006 | Shluzas et al. | |
| 2007/0055281 A1 | 3/2007 | Osorio et al. | |
| 2007/0129669 A1 | 6/2007 | Lin et al. | |
| 2007/0129670 A1 | 6/2007 | Lin et al. | |
| 2007/0156242 A1 | 7/2007 | Lin et al. | |
| 2009/0254132 A1 | 10/2009 | Scribner et al. | |
| 2011/0288528 A1 | 11/2011 | Lin et al. | |
| 2011/0288530 A1 | 11/2011 | Yuan et al. | |
| 2011/0295231 A1 | 12/2011 | Lin et al. | |
| 2013/0197534 A1 | 8/2013 | Lauderbaugh et al. | |

FOREIGN PATENT DOCUMENTS

| | | |
|---|---|---|
| EP | 1 588 674 A1 | 10/2005 |
| EP | 1 588 732 A1 | 10/2005 |
| EP | 1 882 459 A2 | 1/2008 |
| WO | WO 02/26170 A2 | 4/2002 |
| WO | WO 03/057088 A1 | 7/2003 |
| WO | WO 2006/028986 | 3/2006 |
| WO | WO 2007/008721 | 1/2007 |
| WO | WO 2007/008794 | 1/2007 |
| WO | WO 2007/062394 | 5/2007 |
| WO | WO 2009/036466 A1 | 3/2009 |
| WO | WO 2011/075672 | 6/2011 |

OTHER PUBLICATIONS

European Office Action for EP 05794205.4, mailed Oct. 2, 2009.
Chinese Office Action for 200680043269.1, mailed Sep. 25, 2009.
International Search Report for PCT/US2005/031356, mailed Apr. 7, 2006.
Office Action for U.S. Appl. No. 11/674,085, mailed Nov. 4, 2009.
Office Action for U.S. Appl. No. 11/674,085, mailed Apr. 3, 2009.
Office Action for U.S. Appl. No. 11/674,085, mailed Apr. 22, 2008.
Office Action for U.S. Appl. No. 11/674,085, mailed Nov. 29, 2007.
Office Action for U.S. Appl. No. 11/674,085, mailed Jun. 11, 2007.
Office Action for U.S. Appl. No. 10/652,470, mailed Mar. 13, 2006.
Office Action for U.S. Appl. No. 11/674,088, mailed Jun. 8, 2007.
Office Action for U.S. Appl. No. 11/674,088, mailed Nov. 28, 2007.
Office Action for U.S. Appl. No. 11/674,088, mailed Apr. 22, 2008.
Office Action for U.S. Appl. No. 11/674,088, mailed Oct. 24, 2008.
Office Action for U.S. Appl. No. 11/674,088, mailed Jul. 9, 2009.
Office Action for U.S. Appl. No. 11/574,562, mailed May 1, 2009.

(56) References Cited

OTHER PUBLICATIONS

Chinese Office Action for 200580037847.6, mailed Jan. 22, 2010.
Chinese Office Action for 200680043269.1, mailed May 7, 2010.
Office Action for U.S. Appl. No. 11/674,088, mailed Jan. 22, 2010.
Final Office Action for U.S. Appl. No. 11/674,088, mailed Jun. 24, 2010.
Final Office Action for U.S. Appl. No. 11/674,085, mailed Jun. 24, 2010.
U.S. Appl. No. 12/972,001, filed Dec. 17, 2010.
International Search Report and Written Opinion for PCT/US2006/026727, mailed Jan. 29, 2007.
Chinese Office Action for 200680029705.X, mailed Jul. 10, 2009.
Chinese Office Action for 200680029705.X, mailed Dec. 15, 2010.
Office Action for U.S. Appl. No. 11/562,803, mailed Jan. 7, 2009.
Office Action for U.S. Appl. No. 11/674,088, mailed Nov. 12, 2010.
Office Action for U.S. Appl. No. 12/829,500, mailed Nov. 10, 2010.
Office Action for U.S. Appl. No. 13/195,490, mailed Jan. 3, 2013.
Office Action for U.S. Appl. No. 11/562,803, mailed Mar. 8, 2011.
Office Action for U.S. Appl. No. 11/562,803, mailed Mar. 24, 2014.
Office Action for U.S. Appl. No. 13/196,221, mailed Sep. 24, 2012.
Office Action for U.S. Appl. No. 13/196,221, mailed Aug. 1, 2013.
Final Office Action for U.S. Appl. No. 13/196,221, mailed May 15, 2014.
Office Action for U.S. Appl. No. 12/677,939, mailed Sep. 25, 2013.
Office Action for U.S. Appl. No. 13/195,483, mailed Jan. 3, 2013.
Final Office Action for U.S. Appl. No. 11/994,837, mailed Oct. 21, 2011.
Office Action for U.S. Appl. No. 11/994,838, mailed May 24, 2011, 8 pages.
Final Office Action for U.S. Appl. No. 11/994,838, mailed Mar. 14, 2012.
Final Office Action for U.S. Appl. No. 12/204,768, mailed on Apr. 16, 2012.
Office Action for U.S. Appl. No. 12/677,933, mailed Jun. 27, 2012.
Final Office Action for U.S. Appl. No. 12/677,933, mailed Jan. 3, 2013.
Office Action for U.S. Appl. No. 12/972,001, mailed Dec. 26, 2013.
Office Action for U.S. Appl. No. 12/972,001, mailed Sep. 18, 2014.
European Search Report for EP Application No. 06840005.0, mailed Nov. 29, 2011, 11 pages.
Chinese Office Action for 201010525530.X, mailed Apr. 23, 2012, 9 pages.
Chinese Office Action for 201010525530.X, mailed Dec. 5, 2012, 15 pages.
Korean Office Action for 10-2008-7012346, mailed May 3, 2013, 6 pages.
Chinese Office Action for 200580037847.6, mailed Oct. 19, 2011, 6 pages.
Chinese Office Action for 200580037847.6, mailed May 30, 2012, 7 pages.
Office Action for U.S. Appl. No. 10/651,988, mailed Mar. 14, 2006.
Office Action for U.S. Appl. No. 10/949,217, mailed Mar. 9, 2006.
Chinese Office Action for 200680029705.X, mailed Sep. 16, 2010.
International Search Report and Written Opinion for International Application No. PCT/US2008/076463, mailed Dec. 9, 2008.
Office Action for U.S. Appl. No. 11/562,803, mailed on May 14, 2015.
Office Action for U.S. Appl. No. 13/196,221, mailed Mar. 20, 2015.

\* cited by examiner

METHOD FOR INSERTING MEDICINE INTO ANIMAL TISSUE

CROSS-REFERENCE TO RELATED APPLICATIONS

This application is a continuation of U.S. patent application Ser. No. 10/652,470, entitled "Extractable Filler for Inserting Medicine into Animal Tissue," filed Sep. 2, 2003, now U.S. Pat. No. 7,175,628, which claims priority to Taiwanese patent application No. 92113771, filed May, 21, 2003, the disclosure of each of which is hereby incorporated by reference in its entirety.

FIELD OF THE INVENTION

The present invention relates generally to an instrument which is used in the restorative operation of animal tissue disorder. More specifically this surgical instrument can be used to insert a medical material into an animal tissue such that the instrument can be separated from the medical material and drawn out of the animal tissue so as to avert the possibility of tissue rejection.

BACKGROUND OF THE INVENTION

The surgical treatment of animal tissue disorder can be generally attained by one of three methods, which include the hypodermic injection of medicine, the balloon-insertion of medicine, and the filler-insertion of medicine. For example, the U.S. Pat. Nos. 5,972,105; 6,066,154; and 6,248,110B1 disclose respectively a method for treating bone tissue disorders, such as osteoporosis and vertebral compression fractures. The method involves the use of a balloon (made by the Kyphon Crop., U.S.A.) by which the tissue is expanded to facilitate the inserting of the medicine. This balloon method is defective in design in that the medicine is apt to spread aimlessly in the tissue without boundary. Without containment, the medicine is not as effective and there is the possibility of injury to the surrounding tissues.

In order to prevent the drawbacks of the balloon method described above, the filler-insertion method is used to implant the medicine in animal tissue in such a way that the medicine is contained in the filler, and that both the medicine and the filler are implanted in the animal tissue. This filler-insertion method is often carried out in danger of the tissue rejection of the filler.

SUMMARY OF THE INVENTION

The present invention provides an extractable device for inserting a medicinal filling into an animal tissue, said device comprising:

a filling member comprising a flexible and hermetic wall and provided with a holding portion, an injection port at one end of the holding portion, and an opening at another end of the holding portion;

one or more thread, each having one end for fastening releasably said opening of said holding portion in such a manner that said opening is leakproof; and a pasty medicine to be injected into said holding portion via said injection port of said filling member in the wake of a process for inserting said filling member into the animal tissue whereby said pasty medicine solidifies in said holding portion of said filling member;

said opening of said holding portion being unfastened at the time when other end of said threads is pulled by an external force, thereby enabling said filling member to be extracted from the animal tissue so as to leave only said medicine in the animal tissue.

Preferably, said holding portion of said filling member is integrally formed by said flexible and hermetic wall into a body in the form of sac, bag, or ball.

Preferably, said pasty medicine is a mixture of a liquid and a medicinal powdered substance or medicinal granular substance.

Preferably, the device of the present invention further comprises an injection tool for injecting said pasty medicine into said holding portion via said injection port.

Preferably, said injection tool comprises a guide tube and a syringe, wherein one end of said guide tube is connected to said injection port of said filling member and another end of said guide tube is connected to said syringe in which said pasty medicine is held, so that said pasty medicine is able to be injected into said holding portion of said filling member by said syringe via said injection port and said guide tube.

Preferably, said flexible and hermetic wall is a double-layer tubular wall having one end of an inner layer thereof being provided with said injection port of said holding portion, and having another end thereof being a folded double-layer end with said opening of said holding portion, wherein said medicine is released from said filling member by pulling a free end of an outer layer of the double-layer tubular wall to retreat the folded double-layer end, after said opening of said holding portion being unfastened.

Preferably, said one or more thread is between said inner layer and said outer layer of said double-layer tubular wall.

The present invention also discloses a method for implanting a solidified medicine into an animal tissue comprising:

inserting a filling member in a hole of an animal tissue, said filling member comprising a flexible and hermetic wall and provided with a holding portion, an injection port at one end of the holding portion, and an opening at another end of the holding portion, wherein one or more thread is provided and each having one end fastening releasably said opening of said holding portion in such a manner that said opening is leakproof;

injecting a pasty medicine into said holding portion via said injection port of said filling member, whereby said pasty medicine solidifies in said holding portion of said filling member; and unfastening said opening of said holding portion by pulling other end of said threads, thereby enabling said filling member to be extracted from the animal tissue so as to leave only said solidified medicine in the animal tissue.

Preferably, the method further comprising fastening detachably an injection tool with said filling member, so that said pasty medicine is injected into said holding portion via said injection tool. More preferably, said injection tool comprises a guide tube and a syringe, wherein one end of said guide tube is connected to said injection port of said filling member and another end of said guide tube is connected to said syringe in which said pasty medicine is held, wherein said pasty medicine is injected into said holding portion of said filling member by said syringe via said injection port and said guide tube.

The flexible wall of the filling member of the present invention is hermetic and made of a biocompatible or biosynthetic material, such as rubber, elastic plastic, titanium, goat intestine, and the like. The flexible wall can be formed into an object in the form of sac, bag, ball, cylinder or rectangular column integrally or by joining separate pieces.

The filling member of the present invention may contain a ray imaging material, such as a metal wire, by which the precise position of the filling member can be easily located by a ray imaging system, such as an X-ray machine.

The features and the advantages of the present invention will be more readily understood upon a thoughtful deliberation of the following detailed description of the preferred embodiments of the present invention with reference to the accompanying drawings.

DETAILED DESCRIPTION OF THE PREFERRED EMBODIMENTS

Figure 1:
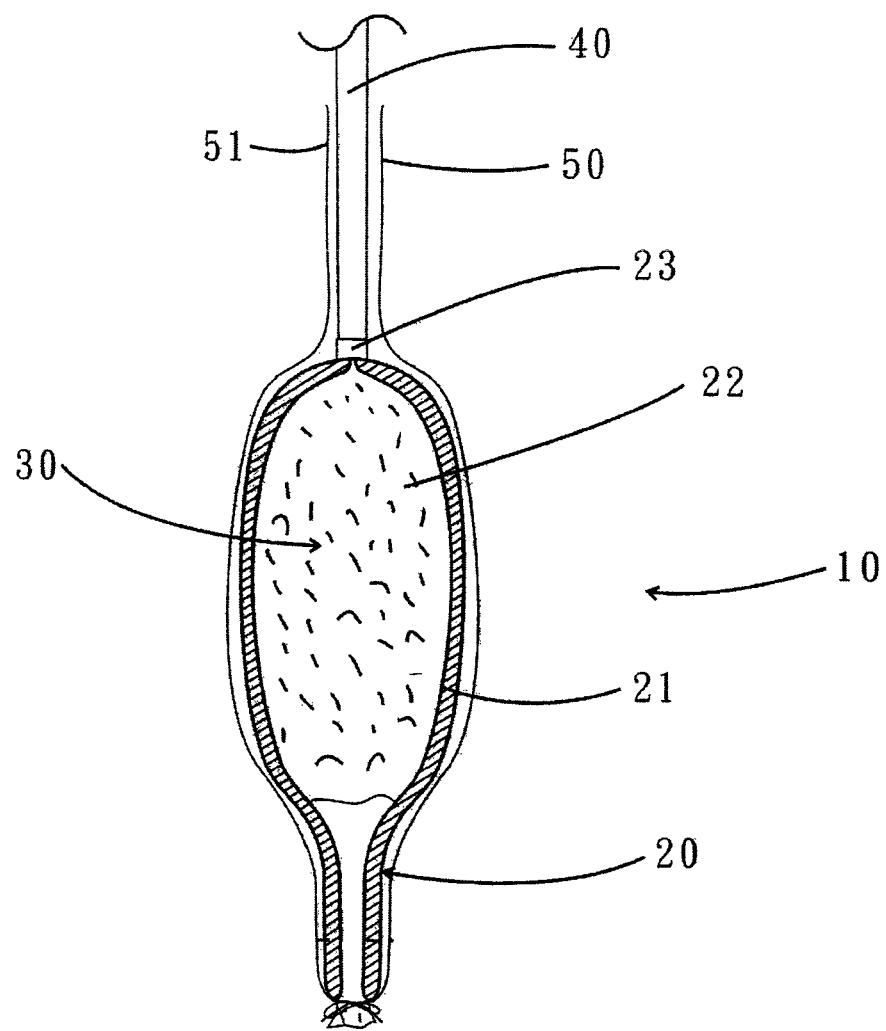
FIG. 1 shows a sectional schematic view of the present invention.

As shown in FIG. 1, an extractable filler 10 embodied in the present invention comprises a filling member 20, a pasty medicine 30, a connection tube 40, and two threads 50 and 51. The filling member 20 is formed of a flexible wall 21 and is provided with a holding portion 22 and an injection port 23. The pasty medicine 30 is injected into the holding portion 22 via the connection tube 40 and the injection port 23. The dotted line 3-3 shows a direction in which a section of the filling member 20 is taken.

Figure 2A:
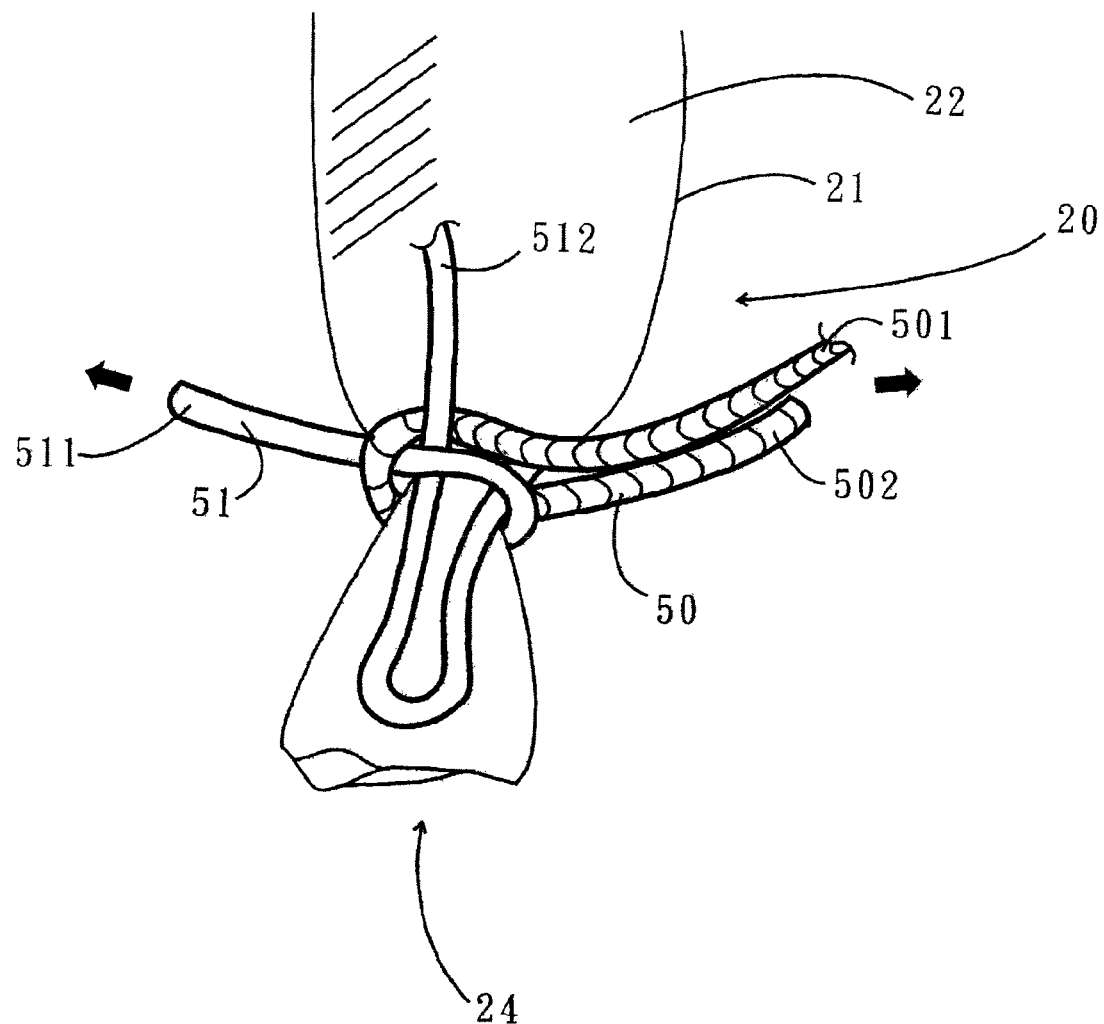
FIGS. 2a-2c are schematic views illustrating the lashing of the opening of the holding portion of the filling member of the present invention.

As shown in FIG. 2a, the holding portion 22 of the filling member 20 is integrally formed of the hermetic flexible wall 21, and is provided with an opening 24 opposite to the injection port 23 of the filling member 20. The filling member 20, for example, is an inflatable rubber balloon with an additional opening like the opening 24. The opening 24 is lashed by two threads 50 and 51. The first thread 50 has a first end 501 and a second end 502, while the second thread 51 has a first end 511 and a second end 512. The two threads 50 and 51 are in fact fastened releasably to the flexible wall 21 near the opening 24. The way by which they are fastened together is not shown in the drawing.

Figure 2B:
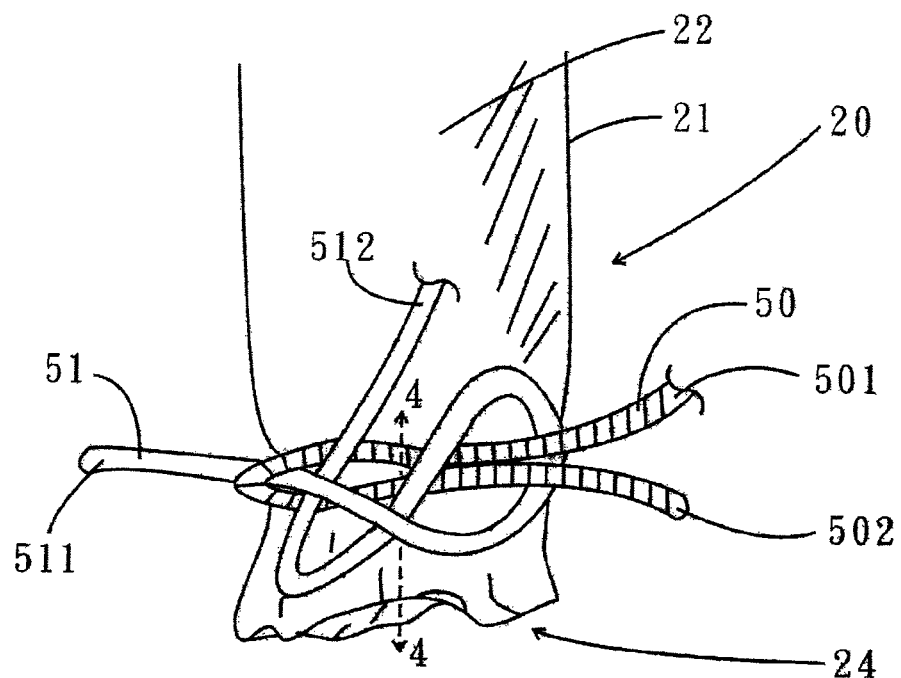
Figure 2C:
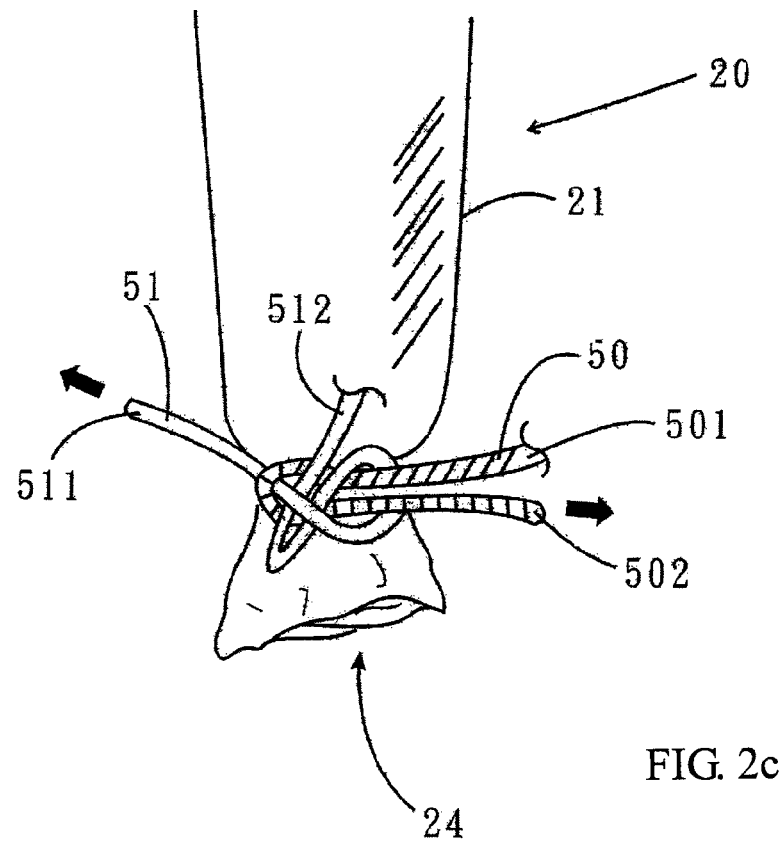

The opening 24 of the holding portion 22 of the filling member 20 is securely tied up to prevent the medicine 30 from leaking out of the holding portion 22 by means of the two threads 50 and 51 which are releasably entangled in such a manner that the first end 511 of the second thread 51 is wound around the first thread 50. Upon completion of the winding process, the flexible wall 21 surrounding the opening 24 is located in a position between the two threads 50 and 51, as indicated by a dotted line 4-4 in FIG. 2b. Thereafter, both ends 501 and 502 of the first thread 50, and the first end 511 of the second thread 51 are respectively pulled rightward and leftwards at the same time, as illustrated in FIG. 2c. As a result, the opening 24 of the filling member 20 is leakproof.

Figure 3A:
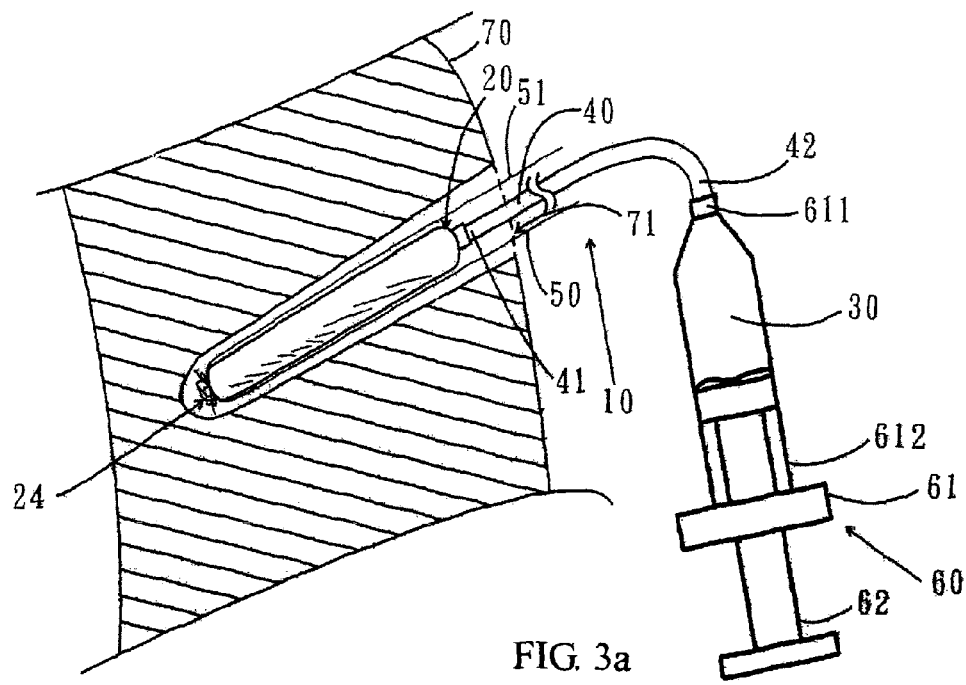
FIGS. 3a and 3b are sectional schematic view of the present invention at work.
Figure 3B:
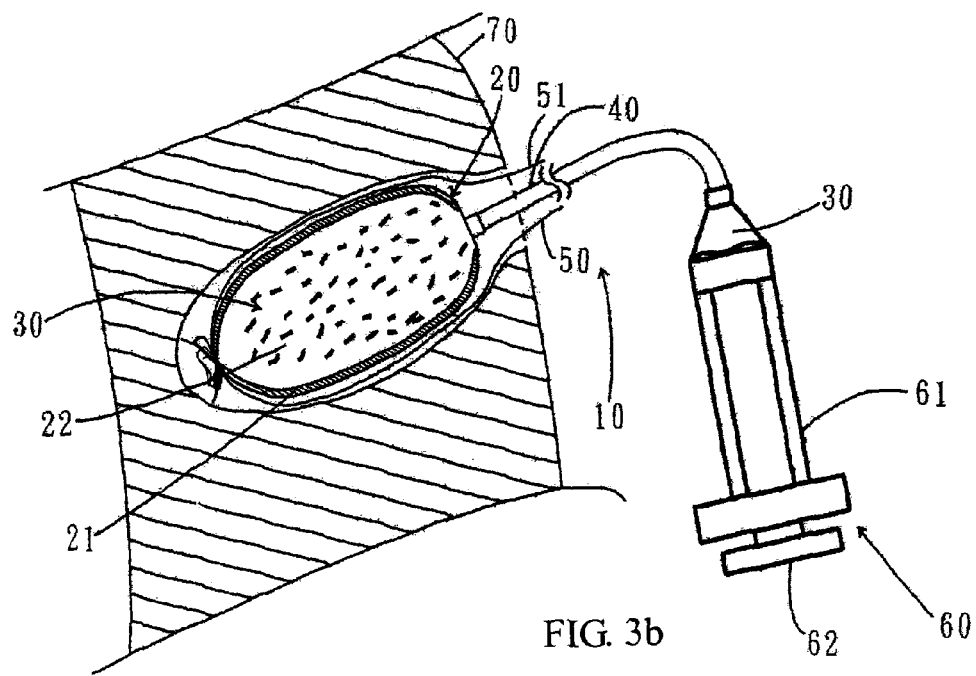

As shown in FIGS. 3a and 3b, the filling member 20 is first inserted into a blind hole 71 of an animal tissue 70. The pasty medicine 30 is then injected into the holding portion 22 of the filling member 20 by a syringe 60 in conjunction with the connection tube 40. The filling member 20 is thus inflated by the medicine 30, as shown in FIG. 3b. The connection tube 40 has one end 41 which is connected with the filling member 20, and another end 42 which is connected to one end 611 of a barrel 61 of the syringe 60. A plunger 62 is slidably inserted into another end 612 of the barrel 61 in which the pasty medicine 30 is contained.

The pasty medicine 30 is a mixture of a liquid and one or more kinds of animal tissue drugs in the form of powder, granule, or colloid. The pasty medicine 30 is capable of solidification.

Figure 4A:
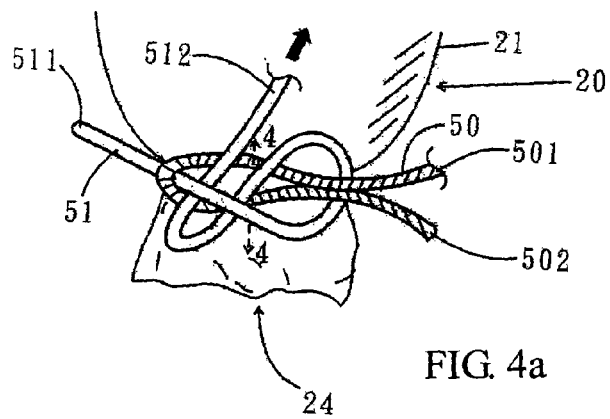
FIGS. 4a-4c are schematic views illustrating the unlashing of the opening of the holding portion of the filling member of the present invention upon completion of the injection of the medicine into the holding portion of the filling member.
Figure 4B:
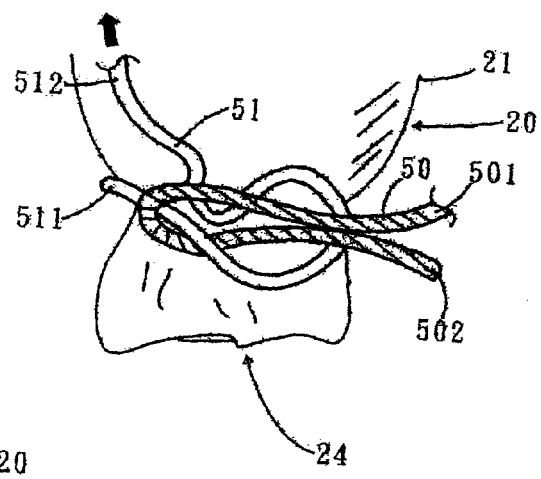
Figure 4C:
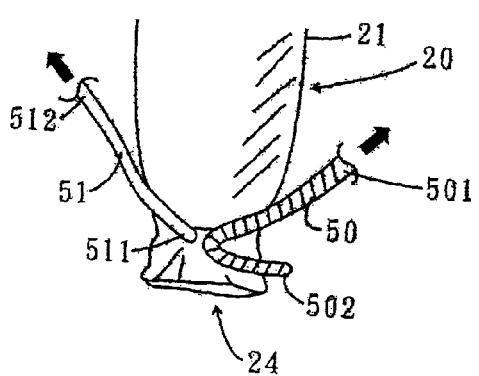

Upon completion of the solidification of the pasty medicine 30 in the blind hole 71 of the animal tissue 70, the filling member 20 must be extracted from the blind hole 71 of the animal tissue 70, so as to leave only the medicine 30 in the blind hole 71 of the animal tissue 70 to prevent the rejection of the filling member 20 by the animal tissue 70. The extraction of the filling member 20 from the blind hole 71 of the animal tissue 70 involves a first step in which the second end 512 of the second thread 51 is pulled upward as indicated by an arrow in FIG. 4a. As a result, the two threads 50 and 51 become loosened, as shown in FIG. 4b. Thereafter, the first end 501 of the first thread 50 and the second end 512 of the second thread 51 are respectively pulled in a direction away from the opening 24 of the filling member 20, as illustrated in FIG. 4c. The opening 24 is thus unfastened completely.

Figure 5A:
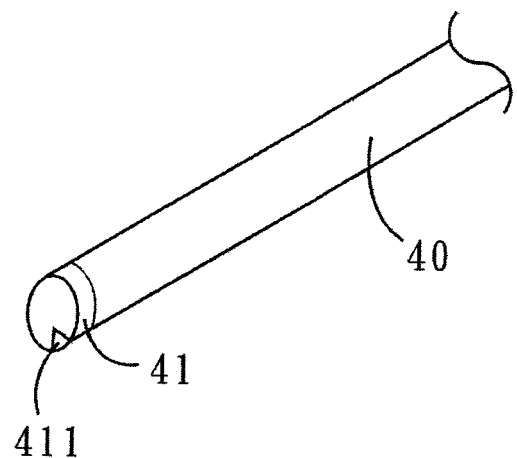
FIG. 5a shows a schematic view of the connection tube of the implantation-injection apparatus of the present invention.
Figure 5B:
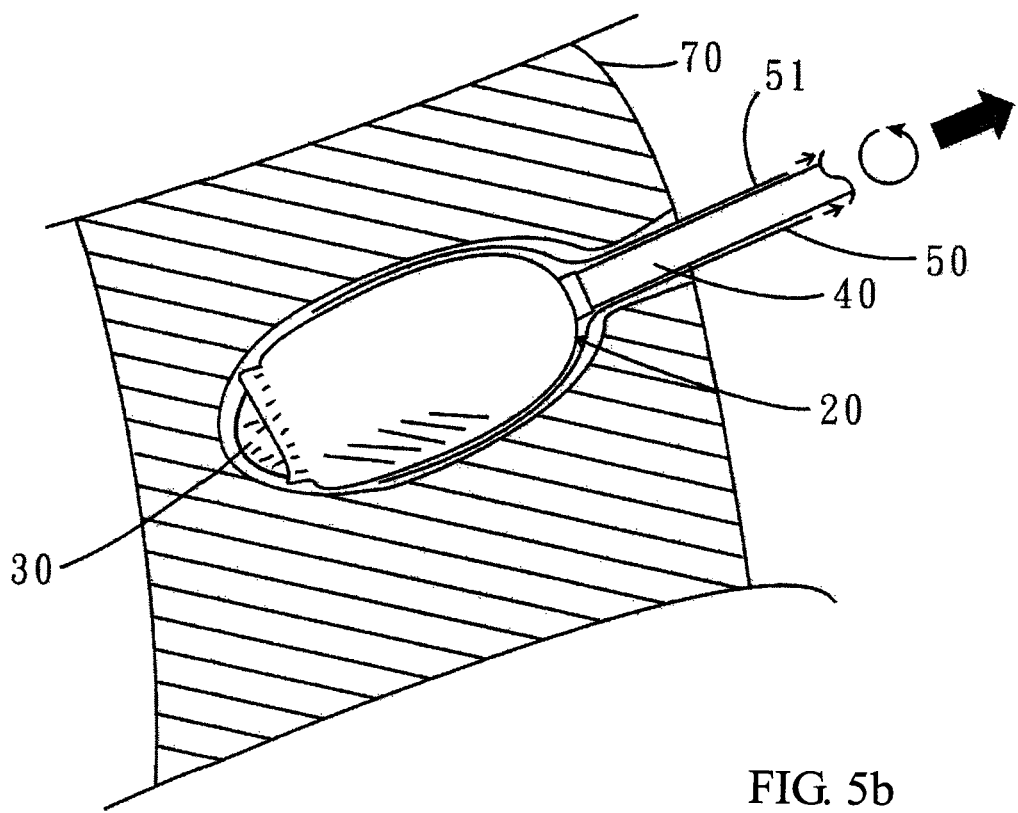
FIGS. 5b and 5c are sectional schematic views illustrating the process in which the filling member of the present invention is extracted from the animal tissue.
Figure 5C:
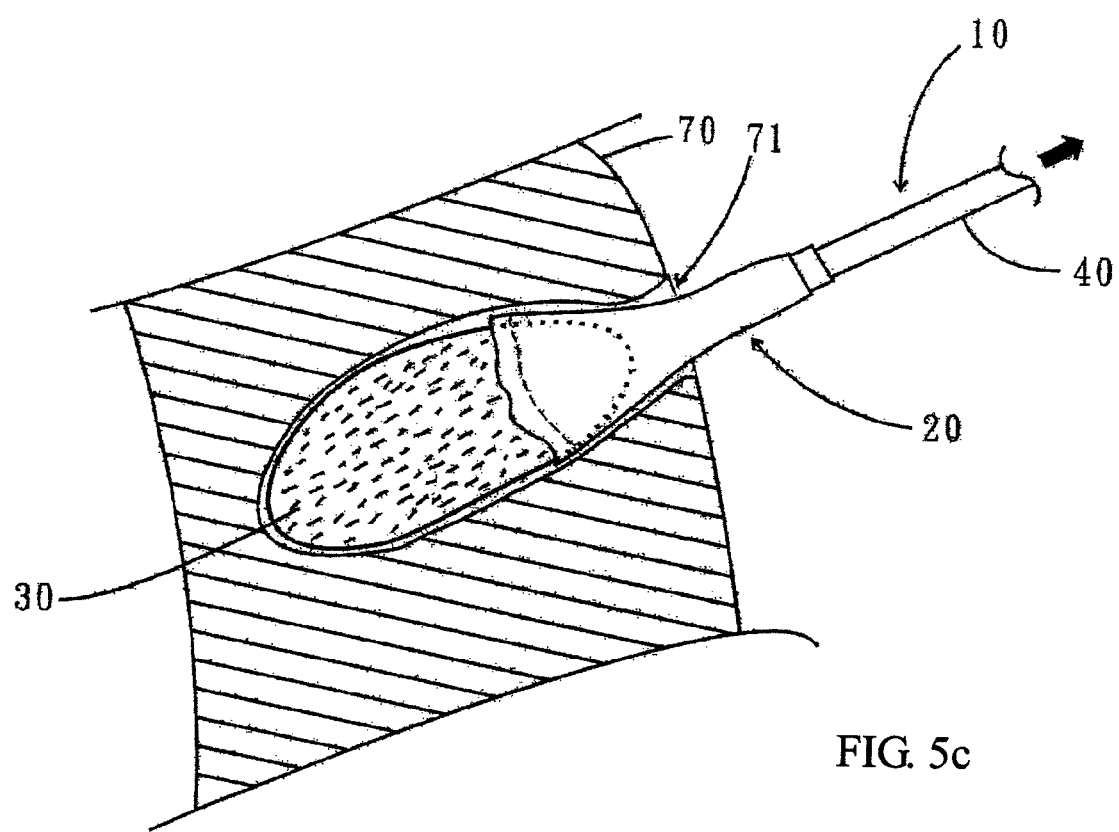

As shown in FIG. 5a, the connection tube 40 is provided in one end 41 with a pointed projection 411 inside the tube. As the connection tube 40 is slightly twisted, the solidified medicine 30 is severed by the pointed projection 411 of the connection tube 40. The filling member 20 can be drawn out of the blind hole 71 of the animal tissue 70 by the connection tube 40, as illustrated in FIG. 5b and FIG. 5c. As a result, only the medicine 30 is left in the blind hole 71 of the animal tissue.

Figure 6A:
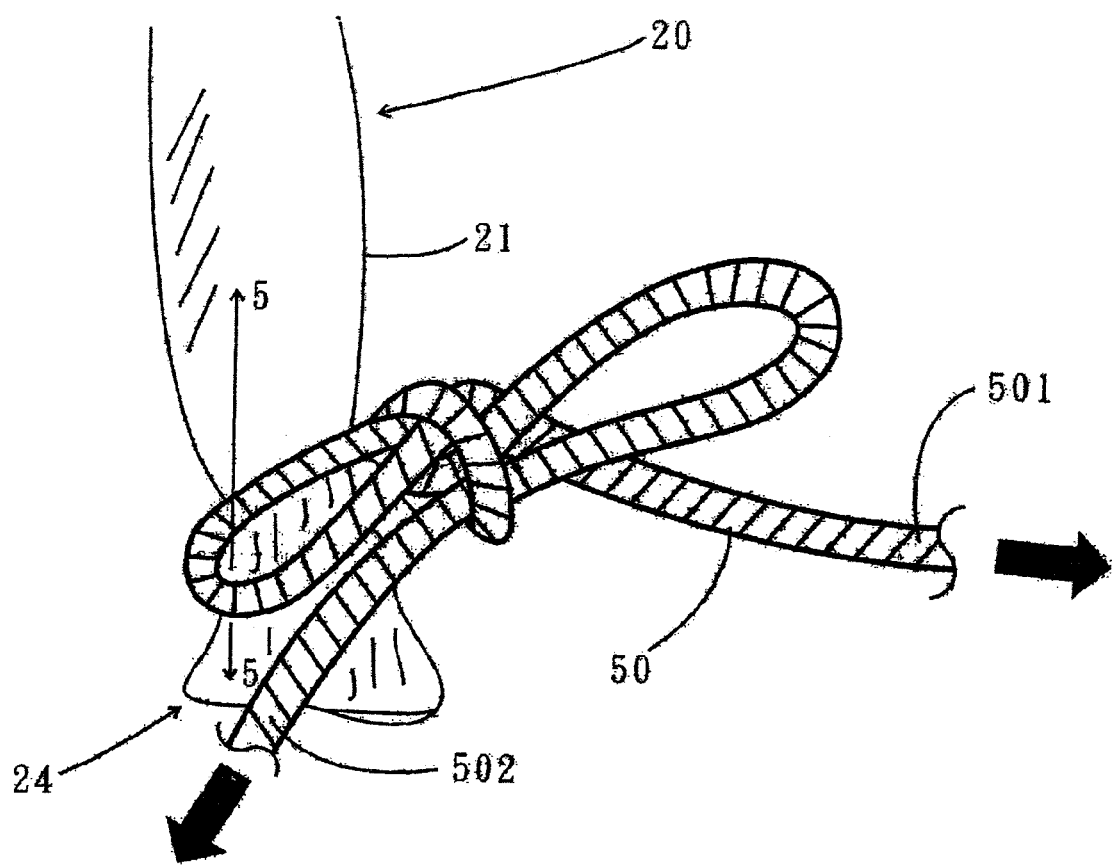
FIGS. 6a and 6b are schematic views illustrating that the opening of the holding portion of the filling member of the present invention is releasably lashed by a thread.
Figure 6B:
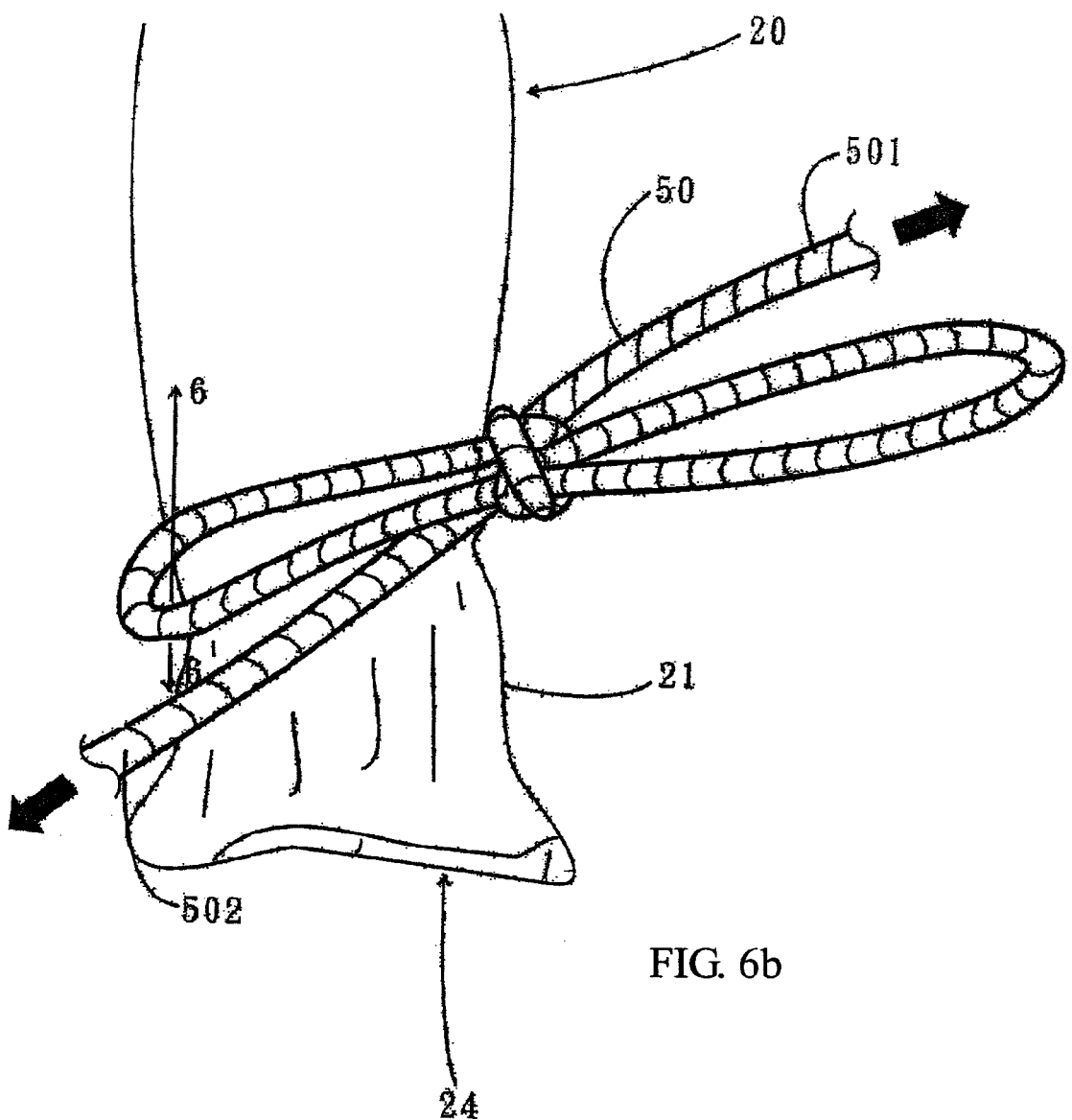

The opening 24 of the filling member 20 may be fastened by only one thread 50, as illustrated in FIGS. 6a and 6b. The thread 50 has a first end 501 and a second end 502. With the thread 50, a knot is formed to lash the opening 24 of the filling member 20 in such a manner that the flexible wall 21 of the opening 24 is surrounded by a loop as indicated by a line 5-5 in FIG. 6a. With the second end 502 of the thread 50 remaining in the stationary state, the first end 501 is pulled to fasten the opening 24. The opening 24 is unfastened by pulling the second end 502 of the thread 20, thereby resulting in separation of the filling member 20 from the thread 50.

The thread 50 can be also used to form a different knot, as shown in FIG. 6b. The flexible wall 21 of the opening 24 of the filling member 20 is surrounded by a loop as indicated by a line 6-6 in FIG. 6b. As the first end 501 of the thread 50 is pulled in a direction away from the filling member 20, the opening 24 of the filling member 20 is lashed to become leakproof. The opening 24 of the filling member 20 is unlashed to enable the filling member 20 to separate from the thread 50 by pulling the second end 502 of the thread 50.

Figure 7A:
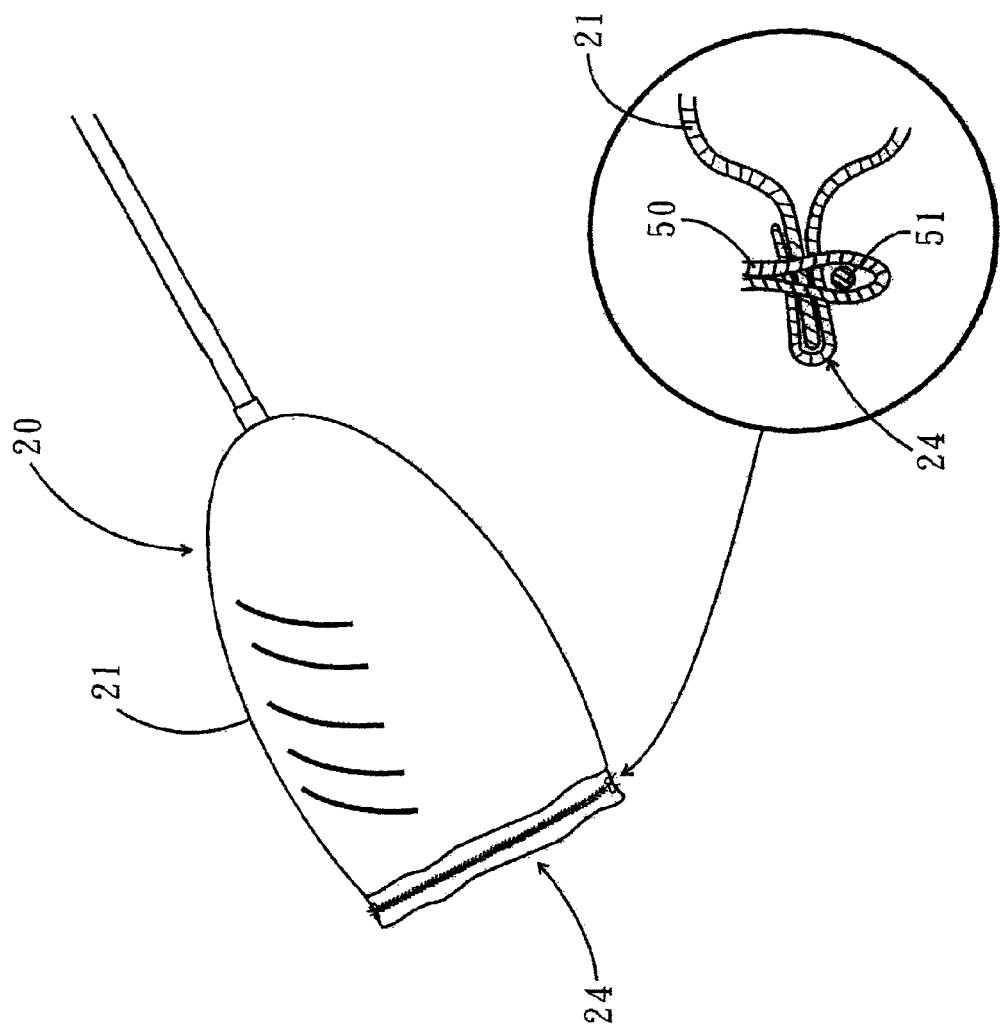
FIGS. 7a-7d are schematic views illustrating a process in which the opening of the holding portion of the filling member of the present invention is releasably lashed by two threads in conjunction with sewing.
Figure 7B:
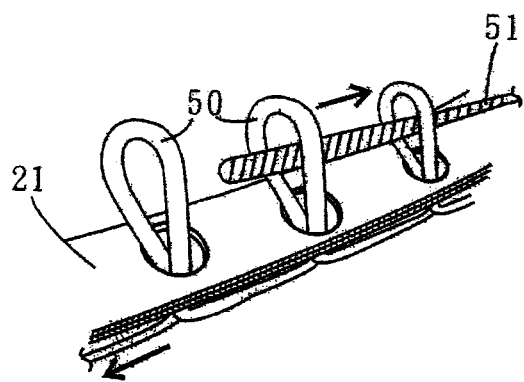
Figure 7C:
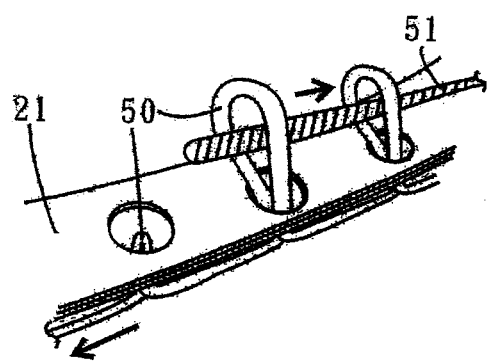
Figure 7D:
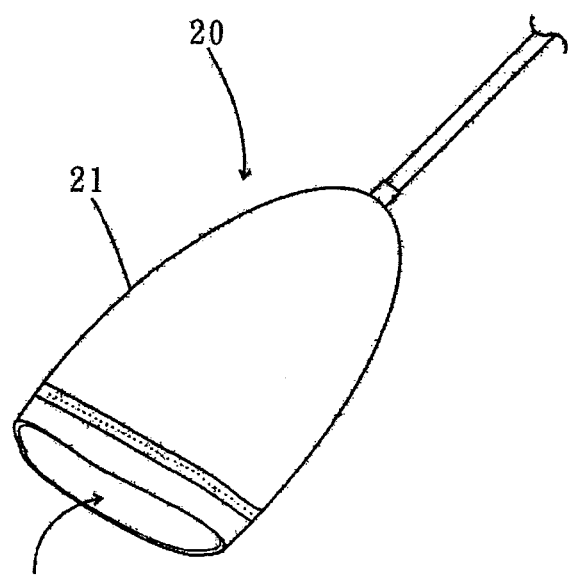

The opening 24 of the filling member 20 can be releasably fastened by sewing in conjunction with two threads 50 and 51, as illustrated in FIGS. 7a-7d. With the first thread 50, a plurality of loops are formed. These loops are joined with the flexible wall 21 of the opening 24 by sewing. The second thread 51 is put through the loops of the first thread 50. As the second thread 51 is pulled out of the loops of the first thread 50, the first thread 50 becomes separated from the flexible wall 21 of the opening 24 of the filling member 20, as illustrated in FIGS. 7b-7d. As a result, the opening 24 is unfastened. Such a fastening as described above is similar to that which is commonly used to fasten the opening of a cement or flour bag.

Figure 8A:
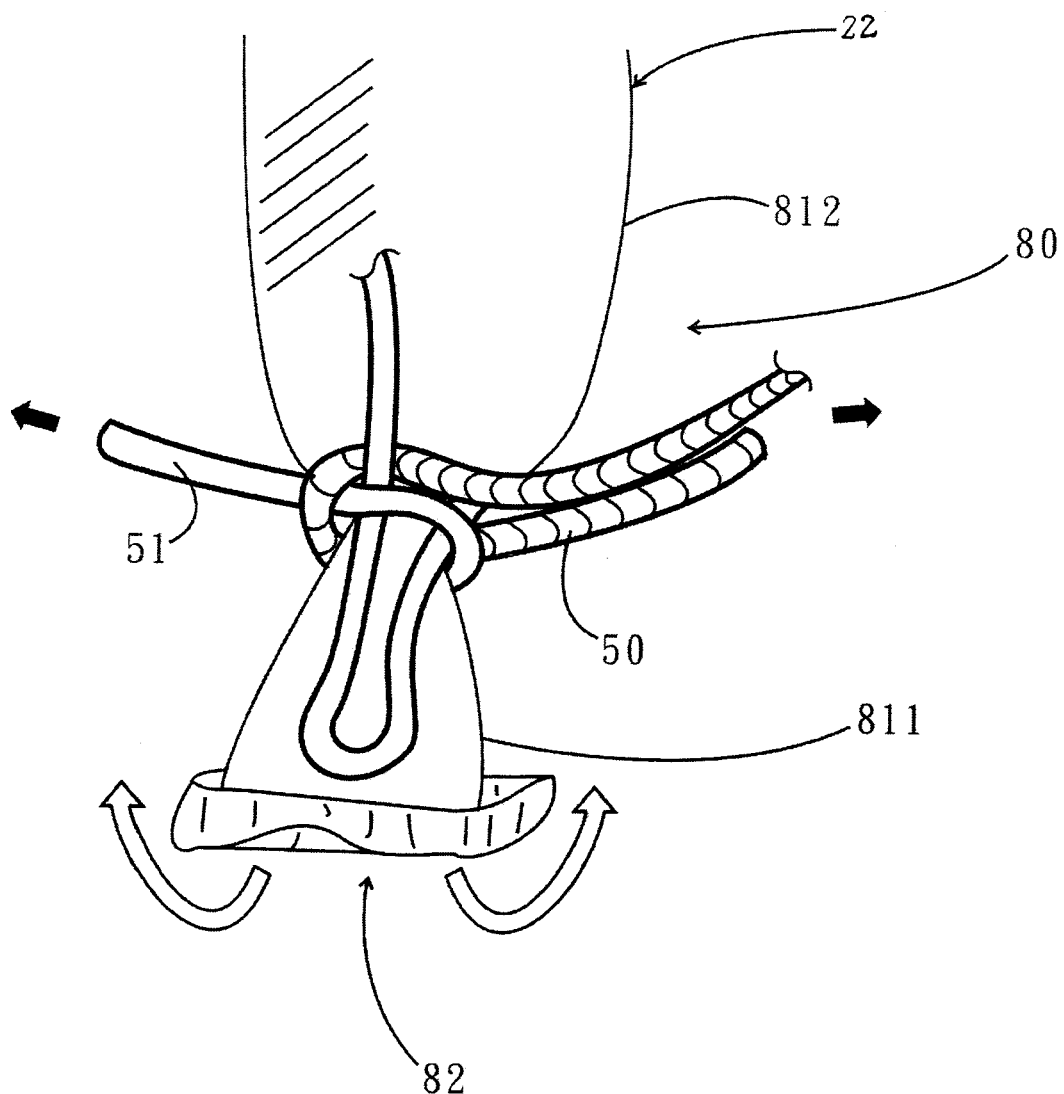
FIG. 8a is a schematic view illustrating a process in which a double-layer wall of the holding portion of the filling member of the present invention is formed.
Figure 8B:
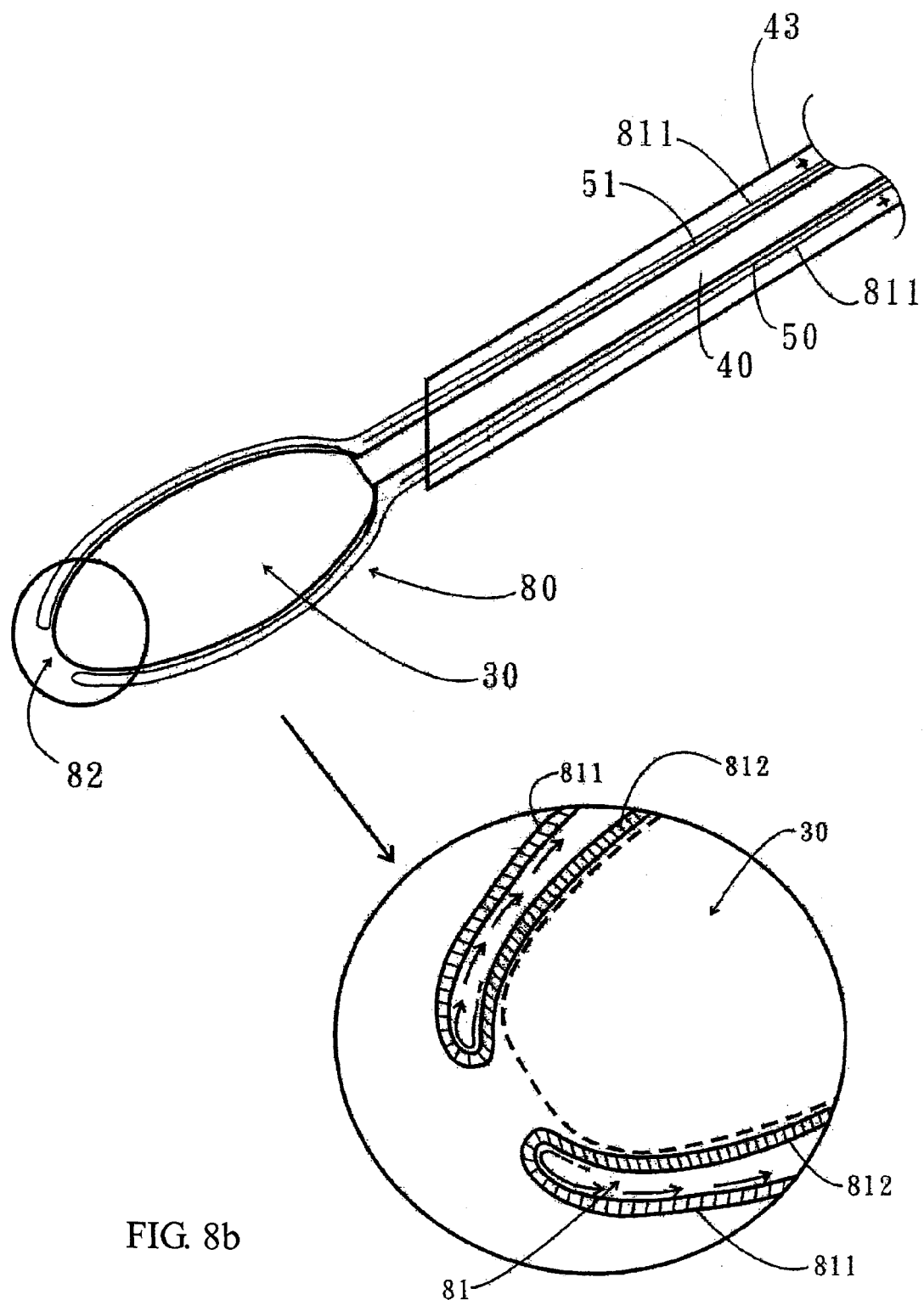
FIG. 8b illustrating a process in which the double-layer wall of the holding portion of the filling member of the present invention is retreated from the solidified medicine.

A further embodiment of the present invention is shown in FIG. 8a, and FIG. 8b, which is similar to the embodiment shown in FIGS. 1 to 2c, except that a filling member 80 is formed of a double-layer wall 81 and the first thread 51 and second thread 52 are located between an inner layer 812 and an outer layer 811 of the double-layer wall 81. As shown in FIG. 8a, a flexible and hermetic tubular wall is tied at an intermediate point thereof by the threads 50 and 51 at the beginning. The lower portion 811 of the tubular wall (will become an outer layer) is then rolled up, so that it is inside out and covering up the threads 50 and 51 and the upper portion 812 of the tubular wall (will become an inner layer). The rolled-up end of said double-layer wall 81 is provided with an opening 82 of the holding portion 22, which is lashed by the two threads 50 and 51. The opening 82 is unfastened by pulling the threads 50 and 51 the same way as shown in FIGS. 4a to 4c. As shown in FIG. 8b, the rolled-up double-layer end is retreated from the solidified medicine 30 by pulling a free end of the outer layer 811 of the double-layer wall 81, while one end of the inner layer 812 is connected to the connection tube 40 as an injection port of said holding portion 22 of the said filling member 80, whereby said solidified medicine 30 is released from said filling member 80. A working tube 43 is used to accommodate the connection tube 40, the threads 50 and 51 and the free end of the outer layer 811 of the double-layer wall 81 of the filling member 80.

The embodiments of the present invention described above are to be regarded in all respects as belong illustrative and nonrestrictive. Accordingly, the present invention may be embodied in other specific forms without deviating from the spirit thereof. The present invention is therefore to be limited only the scopes of the following claims.

The invention claimed is :

1. A method for implanting a solidified medicine into an animal tissue, comprising:
    inserting into the animal tissue a flexible container defining a proximal injection port and a releasably closable distal opening, the proximal injection port and the releasably closable distal opening each being defined by the flexible container prior to the inserting, the releasably closable distal opening being closed during the inserting;
    after the inserting, at least partially filling the container with a solidifiable medicinal filling;
    allowing the medicinal filling to at least partially solidify within the container; and
    extracting the container form the animal tissue when the distal opening of the container is open such that the medicinal filling is removed from the container through the distal opening, the medicinal filling remaining within the animal tissue after the container is extracted.

2. The method of claim 1, further comprising injecting the filling into the container through the proximal injection port.

3. The method of claim 1, further including allowing the medicinal filling to completely solidify after extracting the container.

4. The method of claim 1, wherein the container includes an inner layer and an outer layer.

5. The method of claim 1, wherein at least partially filling the container includes injecting the solidifiable medicinal filling from an injection tool through the proximal injection port of the container.

6. The method of claim 5, further comprising:
    opening the distal opening of the container; and
    injecting an additional amount of the solidifiable medicinal filling into the container after the opening the distal opening of the container.

7. The method of claim 5, further comprising:
    opening the distal opening of the container; and
    injecting an additional amount of the solidifiable medicinal filling into the container after the opening the distal opening of the container and after at least partially extracting the container such that the solidifiable medicinal filling exits the distal opening of the container.

8. The method of claim 1, wherein the extracting includes severing the solidifiable medicinal filling from an injection tool.

9. The method of claim 1, wherein the container is shaped like one of a ball or a bag.

10. The method of claim 1, wherein the flexible container is hermetic.

11. A method for placing a solidified medicine into an animal tissue, comprising:
    inserting into the animal tissue a flexible container having a proximal inlet and a distal outlet, the proximal inlet and the distal outlet each being defined by the flexible container prior to the inserting, the distal outlet being closed during the inserting;
    after the inserting, inserting a solidifiable medicinal filling through the proximal inlet of the container;
    allowing the medicinal filling to at least partially solidify within the container;
    opening the distal outlet of the container;
    disposing the medicinal filling in the animal tissue through the distal outlet; and
    removing the container from the animal tissue.

12. The method of claim 11, further including allowing the solidifiable medicinal filling to further solidify after removing the container from the animal tissue.

13. The method of claim 11, wherein the medicinal filling completely solidifies before disposing the medicinal filling in the animal tissue.

14. The method of claim 11, wherein the distal outlet includes at least one releasable thread configured to releasably seal the distal outlet.

15. The method of claim 14, wherein opening the distal outlet of the container includes applying a pulling force to a first end of the thread.

16. The method of claim 14, wherein the at least one releasable thread includes two releasable threads, and wherein opening the distal outlet of the container includes applying a pulling force to a first end of the first thread and then applying a pulling force to a first end of the second thread.

17. The method of claim 11, wherein the flexible container is hermetic.

18. A method for placing a solidifiable medicine into an animal tissue, comprising:
    inserting into the animal tissue a flexible container having a proximal inlet, a distal outlet, and a holding portion, the proximal inlet and the distal outlet each being defined by the flexible container prior to the inserting;

after the inserting, injecting a solidifiable medicinal filling into the holding portion of the container through the proximal inlet;

allowing the medicinal filling to at least partially solidify within the container;

disposing the filling in the animal tissue through the distal opening by at least partially removing the container from the animal tissue.

19. The method of claim 18, wherein the distal outlet of the container is releasably sealed by at least one thread prior to the inserting.

20. The method of claim 18, further including opening the distal outlet prior to removing the container.

21. The method of claim 18, further including allowing the solidifiable medicinal filling to further solidify after removing the container from the animal tissue.

22. The method of claim 18, wherein the flexible container is hermetic.

* * * * *

UNITED STATES PATENT AND TRADEMARK OFFICE
CERTIFICATE OF CORRECTION

PATENT NO. : 9,113,988 B2
APPLICATION NO. : 11/674087
DATED : August 25, 2015
INVENTOR(S) : Kwan Ku Lin It is certified that error appears in the above-identified patent and that said Letters Patent is hereby corrected as shown below:

In the Specification

Column 5, line 43: "belong" should be --being--.

In the Claims

Column 5, line 49 (claim 1, line 1): "solidified" should be --solidifiable--.

Column 5, line 61 (claim 1, line 13): "form" should be --from--.

Column 6, line 29 (claim 11, line 1): "solidified" should be --solidifiable--.

Signed and Sealed this
Fifth Day of July, 2016

Michelle K. Lee
*Director of the United States Patent and Trademark Office*